United States Patent
Currie et al.

(10) Patent No.: US 6,586,437 B2
(45) Date of Patent: Jul. 1, 2003

(54) (S)-HYDROXYNEFAZODONE ANTIPSYCHOTIC THERAPY

(75) Inventors: Mark G. Currie, Sterling, MA (US); Thomas P. Jerussi, Framingham, MA (US); Paul D. Rubin, Sudbury, MA (US)

(73) Assignee: Sepracor Inc., Marlborough, MA (US)

( * ) Notice: Subject to any disclaimer, the term of this patent is extended or adjusted under 35 U.S.C. 154(b) by 62 days.

(21) Appl. No.: 09/993,130

(22) Filed: Nov. 14, 2001

(65) Prior Publication Data

US 2002/0077326 A1 Jun. 20, 2002

Related U.S. Application Data

(63) Continuation-in-part of application No. 09/545,475, filed on Apr. 7, 2000.
(60) Provisional application No. 60/128,481, filed on Apr. 9, 1999.

(51) Int. Cl.[7] .................. A61K 31/525; A61P 25/24
(52) U.S. Cl. ................................... 514/254.05
(58) Field of Search ..................... 514/254.05

(56) References Cited

U.S. PATENT DOCUMENTS

| | | | |
|---|---|---|---|
| 4,338,317 A | 7/1982 | Temple et al. | 424/250 |
| 4,613,600 A | 9/1986 | Gammans et al. | 514/252 |
| 5,116,852 A | 5/1992 | Gammans | 514/359 |
| 5,256,664 A | 10/1993 | Mayol et al. | 514/252 |
| 5,691,324 A | 11/1997 | Sandyk | 514/159 |
| 5,788,986 A | 8/1998 | Dodman | 424/451 |
| 5,852,020 A | 12/1998 | Marcus et al. | 514/252 |
| 5,854,248 A | 12/1998 | Marcus et al. | 514/255 |

FOREIGN PATENT DOCUMENTS

EP 0769297 A1 4/1997

OTHER PUBLICATIONS

Green et al. "Clinical Pharmacokinetics of Nefazodone" *Clin. Pharmacokinet.* 33, 260–275 (1997).
Barbahaiya et al. "Single and Multiple Dose Pharmacokinetics of Nefazodone in Subjects Classified . . . " *Br. J. Clin. Pharm.* 42, 573–581 (1996).
Cyr et al. "Nefazodone: Its Place Among Antidepressants" *Ann. Pharmacother* 30, 1006–12 (1996).
Malik "Nefazodone: structure, mode of action and pharmacokinetics" *J. Psychopharm.* 10, 1–4 (1996).
S.A. Montgomery "Efficacy of nefazodone in the treatment of depression" *J. Psychopharm.* 10, 5–10 (1996).
Nacca et al. "Brain–to–blood partition and in vivo inhibition of 5–hydroxytryptamine reuptake . . . " *Br. J. Pharmac.* 125, 1617–1623 (1998).
von Moltke et al. "Nefazodone, meta–chlorophenylpiperazine, and their metabolites . . . " *Psychopharma.* 145, 113–122 (1999).
Eison et a. "Nefazodone: Preclinical Pharmacology of a New Antidepressant" *Psychopharma. Bulletin* 26, No. 3, 311–315 (1990).
Joffe et al. "Adjunctive nefazodone in neuroleptic–treated schizophrenic patients with predominantly . . . " *Intl. Clin. Psychopharma.* 14, 233–238 (1999).
Rosenberg et al. "Nefazodone in the Adjunctive Therapy of Schizophrenia: An Open–Label . . . " *Clin. Neuropharma.* 23, 222–225 (2000).

*Primary Examiner*—Richard L. Raymond
*Assistant Examiner*—Hong Liu
(74) *Attorney, Agent, or Firm*—Heslin Rothenberg Farley & Mesiti P.C.

(57) ABSTRACT

Treatment of psychoses with (S)-hydroxynefazodone is disclosed.

7 Claims, No Drawings

(S)-HYDROXYNEFAZODONE ANTIPSYCHOTIC THERAPY

CROSS-REFERENCE TO RELATED APPLICATIONS

This application is a continuation-in-part of copending U.S. application Ser. No. 09/545,475, filed Apr. 7, 2000, which claims the benefit of U.S. Provisional Application 60/128,481, filed Apr. 9, 1999. The entire disclosures of both are incorporated herein by reference.

FIELD OF THE INVENTION

The present invention relates to methods of treating psychoses using (S)-hydroxynefazodone.

BACKGROUND OF THE INVENTION

Clinicians recognize a distinction among mental illnesses—in particular between psychoses (e.g. schizophrenia, dementia, obsessive-compulsive disorder, Tourette's disorder, bipolar disorder and schizoaffective disorder) and psychiatric disorders (e.g. depression, anxiety, social phobia and panic disorder). The two types of mental illnesses are treated quite differently. Psychoses are treated with D2 antagonists, the "typical" antipsychotics and "atypical" antipsychotics. Psychiatric disorders, i.e. mental illnesses other than psychoses, are treated with drugs that inhibit the neuronal reuptake of mono amines, particularly of serotonin, such as SSRI's.

Antipsychotic agents are employed in the treatment of psychoses. All of the common antipsychotic agents are antagonists at post-synaptic $D_2$ receptors, and this is accepted in the art as the mechanism by which they exert their antipsychotic activity. Antipsychotic agents are commonly considered to fall into one of two classes: "typical" and "atypical".

Haloperidol is the archetype of the "typical" antipsychotic. It is an antagonist at post-synaptic $D_2$ receptors, but it is indiscriminate. Dopamine receptors are distributed throughout the nervous system, and in addition to being in cortical areas, both in neocortex and paleocortex (limbic areas), they are also present in areas associated with motor functions, such as the striatum. Blockade of dopamine receptors in the striatum gives rise to many of the side effects associated with the use of haloperidol, the so-called extrapyramidal side effects. Other "typical" antipsychotics include fluphenazine, perphenazine and trifluoperazine.

"Atypical" antipsychotics are differentiated from "typical" by their less acute extrapyramidal side effects, especially dystonias. Clozapine is the prototypical atypical antipsychotic. Other atypical antipsychotics include: olanzapine, risperidone, sertindole, quetiapine and ziprasidone. Neither nefazodone nor hydroxynefazodone has been reported to be effective as an antipsychotic.

The core symptoms of schizophrenia are considered to include hallucinations, agitation and delusions. Typical antipsychotics purely block the $D_2$ receptor and work fairly well for core symptoms. They do very little for the so-called negative or secondary symptoms of schizophrenia, which include apathy, the lack of ability to experience pleasure and the lack of motivation. In fact, these secondary symptoms may be more significant to the overall morbidity of the illness in terms of loss productivity and quality of life than the core symptoms. Because they appear more effective against the secondary symptoms, the atypical antipsychotics are often preferred. In addition to both the core and secondary symptoms of schizophrenia, many persons with schizophrenia also suffer with disturbances of mood and affect that can be clinically significant. As a result, many persons with schizophrenia and schizoaffective disorder are treated with antidepressants for the mood symptoms.

Psychiatric disorders other than psychoses, such as depression, anxiety, social phobia and panic disorder are treated with drugs that inhibit the neuronal reuptake of monoamines (e.g. serotonin, norepinephrine and dopamine). These reuptake inhibitors are referred to collectively as MRI's (monoamine reuptake inhibitors). Selective serotonin reuptake inhibitors (SSRI's) are a particularly preferred subclass of MRI's. The most widely known SSRI's, in addition to nefazodone, are fluoxetine, venlafaxine, milnacipran, citalopram, fluvoxamine, paroxetine, and sertraline.

Nefazodone, the metabolic parent of hydroxynefazodone, is approved for the treatment of depression by the United States Food and Drug Administration. It is available under the trade name SERZONE® from Bristol-Myers Squibb. Studies have shown that nefazodone is extensively metabolized in the body. [See, for example, Green, D. S. and Barbhaiya, R. H., *Drug Disposition,* 1997, 260–275 (1997)]. One of these metabolites is the hydroxylated derivative 2-[3-[4-(3-chlorophenyl)1-piperazinyl] propyl]-5-(1-hydroxyethyl)-2,4-dihydro-4-(phenoxyethyl)-3H-1,2,4-triazol-3-one, I, CAS Registry Number 98159-82-1, also known as hydroxynefazodone.

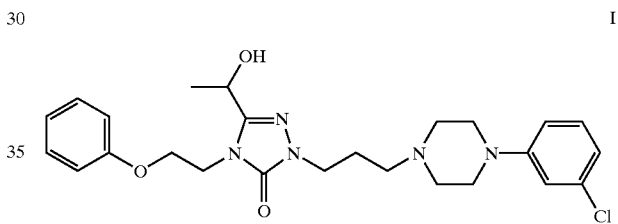

I

The stereochemistry of the metabolite I has not to date been defined in the literature. Use of hydroxynefazodone as an antidepressant is disclosed in U.S. Pat. No. 4,613,600. Neither hydroxynefazodone (racemic) nor either of its stereoisomers is commercially available at the present time. Nefazodone has been shown to antagonize $alpha_1$-adrenergic receptors, a property which may be associated with postural hypotension. In vitro binding studies showed that nefazodone had no significant affinity for the following receptors; $alpha_2$ and beta adrenergic, $5-HT_{1A}$, cholinergic, dopaminergic, or benzodiazepine. Nefazodone hydrochloride is rapidly and completely absorbed, but because of extensive metabolism, its absolute bioavailability is low, about 20%, and variable. Peak plasma concentrations occur at about one hour, and the half-life of nefazodone is 2–4 hours. Nefazodone and hydroxynefazodone exhibit nonlinear kinetics for both dose and time, with AUC and $C_{max}$ increasing more than proportionally with dose increases and more than expected upon multiple dosing over time, compared to single dosing.

While nefazodone can be an effective treatment psychiatric disorders, it can give rise to certain adverse effects. The most frequently reported adverse effects associated with nefazodone are headaches, dry mouth, somnolence, nausea and dizziness. Other adverse affects are headache, asthenia, infection, flu syndrome, chills, fever, neck rigidity, hypotension, pruritus, rash, nausea, constipation, dyspepsia, diarrhea, increased appetite, nausea and vomiting, peripheral edema, thirst, arthralgia, insomnia, lightheadedness, confusion, memory impairment, paresthesia, vasodilatation, abnormal dreams, decreased concentration, ataxia, incoordination, psychomotor retardation, tremor, hypertonia, decreased libido, pharyngitis, cough, blurred vision, abnormal vision, tinnitus, taste perversion, visual field defect, urinary frequency, urinary tract infection, urinary retention, vaginitis and breast pain. In addition, nefazodone is known to cause sinus bradycardia and postural hypotension.

The primary clinical use of nefazodone is in the treatment of depression, but the use of nefazodone for treatment of various other psychiatric disorders has been disclosed in the patent literature. Nefazodone for the treatment of headache disorders is described in U.S. Pat. No. 5,854,248, for the treatment of post traumatic stress disorder, in U.S. Pat. No. 5,852,020, for the treatment of sleep disorders in U.S. Pat. No. 5,116,852, and for treating panic disorders, in European Pat. application EP 769 297. Thus the literature has considered nefazodone effective in treating psychiatric disorders, but not an antipsychotic.

SUMMARY OF THE INVENTION

It has now been discovered that (S)-hydroxynefazodone is an effective treatment for psychoses and secondary features of psychosis including, but not limited to apathy, anhedonia, lack of motivation, depression, agitation, and suicidal ideation.

The present invention relates to a method for treating psychosis. The method comprises administering to a person a need of therapy a therapeutically effective amount of (S)-hydroxynefazodone or a pharmaceutically acceptable salt thereof Psychoses include obsessive-compulsive disorder, dementia, bipolar disorder, mania, schizophrenia and schizoaffective disorder. The use of (S)-hydroxynefazodone results in fewer extrapyramidal side effects and little or no increase in serum prolactin revels, both of which are common when treating psychoses with a $D_2$ receptor antagonist.

DETAILED DESCRIPTION OF THE INVENTION

The present invention relates to a method for treating one or more psychoses by administering (S)-hydroxynefazodone. Hydroxynefazodone contains a single chiral center, and therefore exists in an R- and an S-configuration. Neither of the enantiomers has been described in the literature. The structure of (S)-hydroxynefazodone is shown in Formula II:

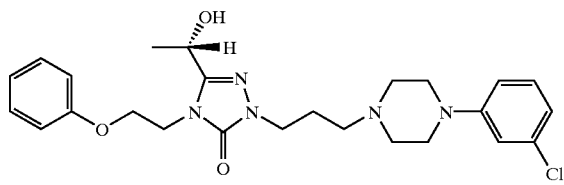

II

The present method encompasses a method which comprises administering the pure (S)-enantiomer. Administration of (S)-hydroxynefazodone results in fewer adverse effects and a broader therapeutic profile compared with administration of a $D_2$ antagonist. One or more of the following adverse effects may be avoided by the administration of (S)-hydroxynefazodone: extrapyramidal symptoms, elevated serum prolactin levels, sexual dysfunction (decreased libido, anorgasmia, ejaculatory dysfunction), breast pain, weight gain and insomnia.

The terms "obsessive-compulsive disorder", "bipolar disorder" and the like are used herein consistent with their accepted meanings in the art. See, e.g., DSM-IV (*Diagnostic and Statistical Manual,* fourth edition). The term "treating" when used in connection with these disorders means amelioration, prevention or relief from the symptoms and/or effects associated with these disorders and includes the prophylactic administration of (S)-hydroxynefazodone to substantially diminish the likelihood or seriousness of the condition.

The magnitude of a prophylactic or therapeutic dose of (S)-hydroxynefazodone will vary with the nature and severity of the condition to be treated and the route of administration. The dose, and perhaps the dose frequency, will also vary according to the age, body weight and response of the individual patient. In general, the total daily dose ranges of (S)-hydroxynefazodone are from about 25 mg per day to about 1000 mg per day, preferably about 100 mg per day to about 600 mg per day, in single or divided doses. It is further recommended that children, patients over 65 years old, and those with impaired renal or hepatic function, initially receive low doses and that the dosage by titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Any suitable route of administration may be employed. For example, oral, rectal, intranasal, and parenteral (including subcutaneous, intramuscular, and intravenous) routes may be employed. Dosage forms include tablets, troches, dispersions, suspensions, solutions, capsules and patches. The pharmaceutical compositions employed in the present invention comprise (S)-hydroxynefazodone or a pharmaceutically acceptable salt thereof as active ingredient, and a pharmaceutically acceptable carrier and, optionally, other therapeutic ingredients. The term pharmaceutically acceptable salts refers to salts prepared from pharmaceutically acceptable non-toxic acids including inorganic acids and organic acids. Exemplary acids that form pharmaceutically acceptable salts with hydroxynefazodone for use in the compositions of the present invention are acetic acid, benzenesulfonic (besylate) acid, benzoic acid, camphorsulfonaic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid and p-toluenesulfonic acid. The hydrochloric acid salt is particularly preferred.

Compositions suitable for oral, rectal, and parenteral administration are encompassed by the present invention. A preferred route of administration is oral. The compositions may be conveniently presented in unit dosage form and prepared by any of the methods well known in the art of pharmacy. Preferred unit dosage formulations are those containing an effective dose, or an appropriate fraction thereof, of the active ingredients.

The compositions of the present invention also include a pharmaceutically acceptable carrier. The carrier may take a wide variety of forms, depending on the forms preparation desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by a standard aqueous or nonaqueous techniques. Oral and parenteral sustained release dosage forms may also be used.

Oral syrups, as well as other oral liquid formulations, are well known to those skilled in the art, and general methods for preparing them are found in any standard pharmacy school textbook, for example *Remington: The Science and Practice of Pharmacy*. Chapter 86 of the 19th edition of Remington entitled "Solutions, Emulsions, Suspensions and Extracts" describes in complete detail the preparation of syrups (pages 1503–1505) and other oral liquids. Similarly, sustained release formulation is well known in the art, and Chapter 94 of the same reference, entitled "Sustained-Release Drug Delivery Systems," describes the more common types of oral and parenteral sustained-release dosage forms (pages 1660–1675.) The relevant disclosure, Chapters 84 and 96, is incorporated herein by reference. Because they reduce peak plasma concentrations, as compared to conventional oral dosage forms, controlled release dosage forms are particularly useful for providing therapeutic plasma concentrations while avoiding the side effects associated with high peak plasma concentrations that occur with conventional dosage forms.

Preparation of the individual enantiomers of hydroxynefazodone is illustrated below in Scheme 1 and the following narrative. Alternatively, the R- and S-isomers of hydroxynefazodone may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step is required to liberate the desired enantiomeric form.

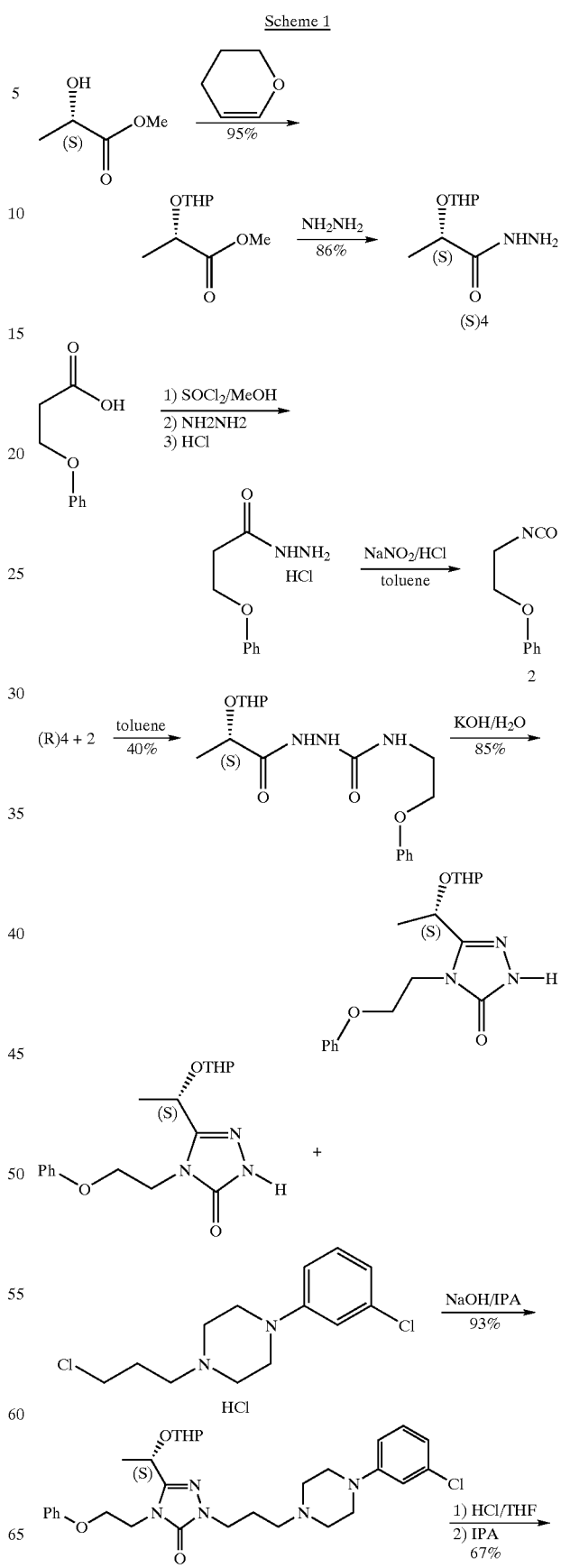

Scheme 1

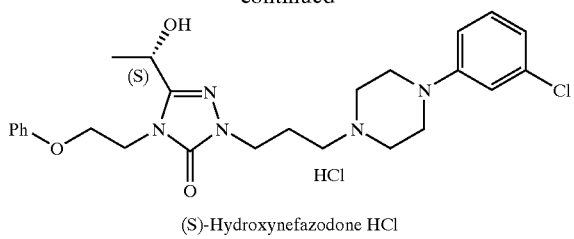

(S)-Hydroxynefazodone HCl (S)-O-(tetryhdropyranyl)-methyl lactate: A 250 mL round bottom flask was equipped with 10.0 g (96 mmol) of (S)-methyl lactate. To the reaction at 23° C. was added 100 mL of CH$_2$Cl$_2$, followed by 13.12 (144 mmol) of dihydropyran and a crystal of TsOH. After stirring for 1 h at rt, the reaction mixture was washed with H$_2$O (2×100 mL). The combined organic phases were dried (MgSO$_4$) and concentrated in vacuo to provide 18.2 g of crude product (100%). $^1$H NMR (CDCl$_3$)δ 1.41–1.89 (m, 9H), 3.46 (m, 1H), 3.76 (s, 3H), 3.89 (m, 1H), 4.34 (m, 1H), 4.72 (m, 1H).

(S)-O-(tetryhdropyranyl)-methyl lactate hydrazide: A 100 mL round bottom flask was charged with 18.0 g of (S)-O-(tetryhdropyranyl)-methyl lactate (95.58 mmol). To the reaction mixture was added MeOH (25 ml ), followed by hydrazine (3.0 mL, 95.58 mmol) at 0° C. and the reaction was allowed to stir overnight. The solution was concentrated in vacuo to remove excess hydrazine and the crude adduct was chromatographed with 100% EtOAc to provide 15.2 g of pure product (84%). $^1$H NMR (CDCl$_3$)δ1.40–1.91 (m, 9H), 3.52 (m, 1H), 3.87 (m, 2H), 4.29 (m, 1H), 4.64 (m, 1H).

Methyl 3-phenoxypropionate: 3-Phenoxypropionic acid (10.0 g, 60 mmol) was dissolved in methanol (100 mL). The reaction mixture was allowed to cool to 0° C. and SOCl$_2$ was slowly added over a 15 min period. The reaction mixture was slowly allowed to warm to room temperature over a 2 h period. The reaction mixture was concentrated in vacuo, then redissolved in ethyl acetate (100 mL). The organic layer was washed with water (2×150 mL), dried (MgSO$_4$), concentrated in vacuo to provide crude product in 95% yield. $^1$H NMR (CDCl$_3$)δ2.84 (t, J=6.4 Hz, 2H), 3.76 (s, 3H), 4.28 (t, J=6.4 Hz, 2H), 6.95 (m, 3H), 7.31 (m, 2H).

3-Phenoxypropionyl Hydrazide: A 100 mL round bottom flask was charged with 17.4 g of methyl 3-phenoxypropionate.(97.1 mmol). To the reaction mixture was added hydrazine (3.65 mL, 116.5 mmol) at rt and the reaction was allowed to stir overnight. The slurry was concentrated in vacuo to remove excess hydrazine and the product was collected by filtration and washed with hexane (25 mL) to provide 14.9 g (86%) of pure product as an off-white solid. $^1$H NMR (CDCl$_3$) δ2.67 (t, J=6.0 Hz, 2H), 3.95 (bs, 2H), 4.27 (t, J=6.0 Hz, 2H), 6.94 (m, 3H), 7.29 (m, 2H).

3-Phenoxypropionyl Hydrazide Hydrochloride: Crude 3-phenoxypropionyl hydrazide (14.6 g, 81.1 mmol) was dissolved in 37 mL of methylene chloride. The solution was stirred at 0° C. as anhydrous IN HCl in ether (89.2 mL, 89.2 mmol) was slowly added. After stirring for 1 h at 0° C., the solid was collected by filtration, rinsed with methylene chloride (2×15.0 mL methylene chloride), and dried in vacuo. The solid weighed 15.2 g (85%). $^1$H NMR (DMSO-D$_6$)δ 2.72 (t, J=5.4 Hz, 2H), 4.20 (t, J=5.4 Hz, 2H), 6.91 (m, 3H), 7.26 (m, 2H).

2-Phenoxyethyl isocyanate: A slurry of 3-phenoxypropionyl hydrazide hydrochloride (10.0 g, 46.12 mmol), 3.83 mL (46.2 mmol) of 37% HCl, 41.1 mL of H$_2$O, and 24.1 mL of toluene was stirred in an ice bath as a solution of 3.50 g (50.7 mmol) of sodium nitrate in 14.1 mL of H$_2$O was added over 20 minutes. The reaction temperature was not allowed to exceed 18° C. After 20 min, the mixture was filtered and the organic phase separated. The aqueous layer was extracted with 8 mL of toluene. The combined organic layers were dried over anhydrous MgSO$_4$. The dried toluene layer was slowly added over a 1 h period with stirring to an empty flask heated at 85° C. When the addition was complete and nitrogen evolution has stopped (bubbling stops), the solution was cooled to rt. $^1$H NMR (CDCl$_3$) δ3.65 (t, J=10.2 Hz, 2H), 4.07 (t, J=10.2 Hz, 2H), 6.96 (m, 3H), 7.29 (m, 2H).

1-((2S)-O-tertahydropyranyl)-propionyl-4-(2-phenoxyethyl)semicarbazide: A 250 mL round bottom flask was charged with 9.55 g of 2-Phenoxyethyl isocyanate (58.6 mmol) and toluene (40 mL). The reaction was cooled to 0° C. and charged with neat (S)-O-(tetryhdropyranyl)-methyl lactate hydrazide (11.01 g, 58.6 mmol). The reaction was allowed to slowly warm to rt overnight. The next morning, the solution was concentrated in vacuo and chromatographed with 100% EtOAc to provide 7.3 g (36%) of pure product as an oil. $^1$H NMR (CDCl$_3$) δ1.40–1.98 (m, 9H), 3.53 (m, 3H), 3.99 (m, 3H), 4.30 (m 1H), 4.64 (m, 1H), 6.17 (m, 1H), 6.89 (m, 3H), 7.25 (m, 2H), 7.86 (bs, 1H), 8.44 (bs, 1H), 8.56 (bs, 1H).

5-[(1S)-1-(tetrahydropyran-2-yl)oxyethyl)-4-(2-phenoxyethyl)-2H-1,2,4-triazol-3(4H)-one: A 250 mL round bottom flask was charged with 7.2 g of 1-((2S)-O-tertahydropyranyl)-propionyl-4-(2-phenoxyethyl) semicarbazide (20.5 mmol). To the reaction mixture was added 110.8 mL of water, followed by solid KOH (1.20 g, 21.5 mmol). The reaction was warmed to 95° C. and allowed to stir for 6 h. The solution was cooled to 0° C. and treated with 37% aqueous HCl solution and 100 mL of dichloromethane. The phases were separated and the organic phase was washed with water, dried (MgSO$_4$), filtered, and concentrated in vacuo to provide crude product. The product was purified by chromatography with 75% EtOAc/hexane to 100% EtOAc to provide 5.5 g (80%) of pure product. $^1$HNMR (CDCl$_3$) δ1.52–1.84 (m, 9H), 3.49 (m, 1H), 3.85 (m, 1H), 4.26 (m, 4H), 4.75 (m, 1H), 5.05 (m, 1H), 6.94 (m, 1H) 7.28 (m, 2H), 10.05 (bs, 1H).

(S)-2-{3-[4-(3-Chlorophenyl)-1-piperazinyl]propyl}-4-(2-phenoxyethyl)-5-[1-(tetrahydropyran-2-yloxy)-ethyl]-2,4-dihydro-[1,2,4]triazol-3-one: A mixture of 40.0 g (120.0 mmol) of 5-((1S)-O-tetrahydropyranyl)-4-(2-phenoxyethyl)-2H-1,2,4-triazol-3(4H)-one, 40.8 g (132.0 mmol) 1-(3-chlorophenyl)-4-(3-chloropropyl)piperazine hydrochloride, 13.91 mL (264.0 mmol) of 50% aqueous sodium hydroxide and 162 mL of 2-propanol was stirred and heated at reflux for 5.5 h. The mixture was filtered hot. The filtrate was concentrated in vacuo and chromatographed with 100% EtOAc to provide 61.1 g (93%) of pure product as an oil. $^1$H NMR (CDCl$_3$) δ1.51 (m, 3H), 1.62 (d, J=9.1 Hz, 3H), 1.71–1.81 (m, 2H), 1.98 (t, J=7.2Hz, 3H), 2.45 (t, J=7.2 Hz, 3H), 2.56 (m, 4H), 3.18 (m, 4H), 3.49 (m, 1H), 3.87 (m, 3H), 4.25 (m, 4H), 4.74 (m, 1H), 5.02 (m, 1H), 6.87 (m, 6H), 7.16 (m, 1H), 7.25 (m, 2H).

(S)-2-{3-[4-(3-Chlorophenyl)-1-piperazinyl]propyl}-4-(2-phenoxyethyl)-5-[1-(hydroxy)-ethyl]-2,4-dihydro-[1,2,4]triazol-3-one ((S)-hydroxynefazodone): A solution of 61.0 g (112 mmol) of 2-[3-[4-(3-Chlorophenyl)-1-piperazinyl] propyl]-5-((1S)-O-tetrahydropyranyl)-4-(2-phenoxyethyl)-2H-1,2,4-triazol-3(4H)-one in 350 mL of THF was treated with 350 mL of 3N HCl at rt. After stirring for 1 h, the solution was concentrated in vacuo and treated with 50% aqueous NaOH solution until pH to 10. The aqueous solution was extracted with dichloromethane (400 mL×2). The organic phase was washed with water (300 mL), dried (MgSO$_4$) and concentrated in vacuo. The crude adduct was chromatographed with 2% MeOH/EtOAc to 4% MeOH/EtOAc to provide 51.1 g (93%) of pure product. $^1$H NMR (CDCl$_3$) δ1.30 (bs, 1H), 1.65 (d, J=10.5 Hz, 3H), 1.99 (t, J=10.2 Hz, 2H), 2.47 (t, J=7.2Hz, 2H), 2.58 (m, 4H), 3.19 (m, 4H), 3.89 (t, J=10.2 Hz, 2H), 4.18 (m, 1H), 4.26 (m, 3H), 5.05 (q, j=10.5 Hz, 1H), 6.87 (m, 5H), 7.03 (m, 1H), 7.16 (m, 1H), 7.26 (m, 2H).

(S)-2-{3-[4-(3-Chlorophenyl)-1-piperazinyl]propyl}-4-(2-phenoxyethyl)-5-[1-(hydroxy)-ethyl]-2,4-dihydro-[1,2,4]triazol-3-one Hydrochloride ((S)-hydroxynefazodone hydroxychloride): A solution of 2-[3-[4-(3-chlorophenyl)-1-piperazinyl]propyl]-5-((1S)-hydroxyl)-4-(2-phenoxyethyl)-2H-1,2,4-triazol-3 (4H)-one (51.1 g, 104.9 mmol) in 567 mL of MTBE was slowly charged with 78.0 mL (157.0 mmol) of 2N HCl over a 15 min. period. After stirring for 1.5 h at 0° C., the slurry was filtered in vacuo to provide 44.0 g (80%) of (S)-hydroxynefazodone HCl as a white solid. The white solid was dissolved in 49 mL of refluxing IPA and slowly allowed to cool to rt. The white solids were collected by filtration to provide 37.3 g (84% recovery) of (S)-hydroxynefazodone HCl as a white solid (99.39% chemical purity, 98.66% ee). The ee was determined by chiral HPLC (Chiralcel OD, 10 um, 4.6×250 nm, hexane/IPA/MeOH/diethyl amine 85:10:5:0.1, 1 mL/min, 230 nm, ambient temperature, (S)-isomer 12.89 min, (R)-isomer 14.47 min). Optical rotation [α]=−32.81° (c. 1.02, MeOH). $^1$H NMR (DMSO-D$_6$) δ1.47 (bs, 3H), 2.11 (m, 2H), 3.14 (m, 4H), 3.50 (m, 4H), 3.76 (m, 4H), 4.17 (m, 4H), 4.80 (m, 1H), 6.92 (m, 6H), 7.29 (m, 3H). $^{13}$C: δ20.62, 23.70, 42.67, 45.50, 51.11, 53.62, 61.24, 65.42, 115.02, 115.92, 119.18, 119.88, 121.63, 124.29, 130.28, 131.32, 133.49, 134.65, 136.07, 149.31, 151.51, 151.57, 154.08, 158.65. MS m/z 485.94. Anal. Calcd for $C_{25}H_{33}Cl_2N_5O_3$: C, 57.47; H, 6.37; N, 13.40. Found: C, 57.01; H, 6.39; N, 13.38.

(R)-Hydroxynefazodone hydrochloride: (R)-Hydroxynefazodone hydrochloride (29.5 g, 98.5% ee, 99.42% chemical purity) was prepared from the (R)-methyl lactate followed the procedure described above for the (S)-isomer. [α]=+32.5 (c. 2, MeOH).

Dopamine and serotonin receptor binding assays were performed in a standard manner with the incubation of membrane preparations in an assay buffer in the presence of a known radioactively labeled specific ligand for the receptor subtypes. Nonspecific binding was determined by assessing binding in the presence of excess ligand. Specific binding was measured as the total labeled ligand bound after the nonspecific binding was subtracted. The effect of the tested agents was measured by determining the competition for the receptor binding across a concentration range. Subsequently, an IC$_{50}$ was determined for the agents tested. More specific details are provided below for several of the assays performed.

Human D$_2$ Receptor

Aliquots of transfected A9L cell membrane preparations corresponding to 20–40 μg protein are incubated for 60 min at 22° C. in 250 μl of 50 mM Tris-HCl buffer (pH 7.4) containing 120 mM NaCl, 5 mM KCl, 5 mM MgCl$_2$, 1 mM EDTA, 0.3 nM [$^3$H]spiperone and increasing concentrations of the competing drugs. Nonspecific binding is determined in the presence of 10 μM (+)butaclamol. After incubation, the samples are filtered rapidly under vacuum through glass fiber filters (GF/B, Packard) and rinsed several times with ice-cold 50 mM Tris-HCl using a cell harvester (Packard). Bound radioactivity is measured with a scintillation counter (Topcount, Packard) using a liquid scintillation cocktail (Microscint 0, Packard). The reference compound for this assay is (+)butaclamol.

Human D$_{4.4}$ Receptor

Aliquots of transfected CHO cell membrane preparations corresponding to 100 μg protein are incubated for 60 min at 22° C. in 250 μl of 50 mM Tris-HCl buffer (pH 7.4) containing 120 mM NaCl, 5 mM KCl, 5 mM MgCl$_2$, 1 mM EDTA, 0.3 nM [$^3$H]spiperone and increasing concentrations of the competing drugs. Nonspecific binding is determined in the presence of 10 μM (+)butaclamol. After incubation, the samples are filtered rapidly under vacuum through glass fiber filters (GF/B, Packard) and rinsed several times with ice-cold 50 mM Tris-HCl using a cell harvester (Packard). Bound radioactivity is measured with a scintillation counter (Topcount, Packard) using a liquid scintillation cocktail (Microscint 0, Packard). The reference compound for this assay is clozapine.

Human 5-HT$_{1A}$ Receptor

Aliquots of transfected CHO cell membrane preparations corresponding to 7–15 μg protein are incubated for 60 min at 22° C. in 250 μl of 50 mM Tris-HCl buffer (pH 7.4) containing 10 mM MgSO$_4$, 0.5 mM EDTA, 0.3 nM [$^3$H]8-OH-DPAT and increasing concentrations of the competing drugs. Nonspecific binding is determined in the presence of 10 μM 8-OH-DPAT. After incubation, the samples are filtered rapidly under vacuum through glass fiber filters (GF/B, Packard) and rinsed several times with ice-cold 50 mM Tris-HCl using a cell harvester (Packard). Bound radioactivity is measured with a scintillation counter (Topcount, Packard) using a liquid scintillation cocktail (Microscint 0, Packard). The reference compound for this assay is 8-OH-DPAT.

Human 5-HT$_{2A}$ Receptor

Aliquots of transfected CHO cell membrane preparations corresponding to 20–50 μg protein are incubated for 15 min at 37° C. in 250 μl of 50 mM Tris-HCl buffer (pH 7.4) containing 2 nM [$^3$H]ketanserin and increasing concentrations of the competing drugs. Nonspecific binding is determined in the presence of 1 μM ketanserin. After incubation, the samples are filtered rapidly under vacuum through glass fiber filters (GF/B, Packard) and rinsed several times with ice-cold 50 mM Tris-HCl using a cell harvester (Packard). Bound radioactivity is measured with a scintillation counter (Topcount, Packard) using a liquid scintillation cocktail (Microscint 0, Packard). The reference compound for this assay is ketanserin.

Human 5-HT$_{2C}$ Receptor

Aliquots of transfected CHO cell membrane preparations corresponding to 5–10 μg protein are incubated for 30 min at 37° C. in 250 μl of 50 mM Tris-HCl buffer (pH 7.7) containing 10 μM pargyline, 0.7 nM [$^3$H]mesulergine and increasing concentrations of the competing drugs. Nonspecific binding is determined in the presence of 1 μM mesulergine. After incubation, the samples are filtered rapidly under vacuum through glass fiber filters (GF/B, Packard) and rinsed several times with ice-cold 50 mM Tris-HCl using a cell harvester (Packard). Bound radioactivity is measured with a scintillation counter (Topcount, Packard) using a liquid scintillation cocktail (Microscint 0, Packard). The reference compound for this assay is mesulergine.

Human 5-HT$_3$ Receptor

Aliquots of transfected HBEK-293 cell membrane preparations corresponding to 3–5 µg protein are incubated for 60 min at 22° C. in 250 µl of 50 mM Tris-HCl buffer (pH 7.4) containing 5 mM MgCl2, 1 mM EDTA, 0.5 nM [$^3$H]BRL 43694 and increasing concentrations of the competing drugs. Nonspecific binding is determined in the presence of 10 µM MDL 72222. After incubation, the samples are filtered rapidly under vacuum through glass fiber filters (GF/B, Packard) and rinsed several times with ice-cold 50 mM Tris-HCl using a cell harvester (Packard). Bound radioactivity is measured with a scintillation counter (Topcount, Packard) using a liquid scintillation cocktail (Microscint 0, Packard). The reference compound for this assay is MDL 72222.

Guinea-pig 5-HT$_4$ Receptor

Aliquots of guinea-pig striatum membrane preparations corresponding to 600 µg protein are incubated for 30 min at 22° C. in 1 ml of 50 mM Hepes-Tris buffer (pH 7.4) containing 0.1 nM [$^3$H]GR 113808 and increasing concentrations of the competing drugs. Nonspecific binding is determined in the presence of 30 µM 5-HT. After incubation, the samples are filtered rapidly under vacuum through glass fiber filters (Filtermat B, Wallac) and rinsed several times with ice-cold 50 mM Hepes-Tris using a cell harvester (Tomtec). Bound radioactivity is measured with a scintillation counter (Betaplate, Wallac) using a solid scintillant (MeltiLex B/HS, Wallac). The reference compound for this assay is 5-HT.

Experimental Conditions for Monoamine Uptake Assays Serotonin Uptake Functional Assay Characterization of serotonin uptake is performed using synaptosomes isolated in a 0.32 M sucrose buffer from a male Wistar rat cortex. The uptake of radiolabelled serotonin by synaptosomes (100 µg of proteins/point) is allowed by incubating them for 15 minutes at 37° C. in presence of test compounds and [3H]5-hydroxytryptamin (0.1 µCi/point). The experiment is performed in a deep well.

Synaptosomes and [3H]5-hydroxytryptamin are prepared in a Krebs buffer pH 7.4 containing 25 mM NaHCO$_3$, 11 mM glucose and 50 µM ascorbic acid. This incubation buffer is oxygenated during 5 minutes before incubation. Basal control is incubated for 15 minutes at 4° C. in order to avoid any uptake. Following this incubation the uptake is stopped by filtration through an "unifilter 96-wells GFB " Packard plate washed with Krebs buffer containing 25 mM NaHCO$_3$ in order to eliminate the free [3H]5-hydroxytryptamin. The radioactivity associated to the synaptosomes retained onto the unifilter corresponding to the uptake is then measured with a microplate scintillation counter Topcount, Packard using a scintillation liquid microscint 0, Packard.

The reference compound is imipramin tested at 10 concentrations ranging from $10^{-11}$ M to $10^{-5}$ M in order to obtain an IC$_{50}$ value. [See Perovics and Müller "Pharmacological profile of hypericum extract: effect on serotonin uptake by postsynaptic receptors", Arzeim. Forsch./Drug Res. 45 :1145–1148 (1995).]cl Dopamine Uptake Functional Assay Characterization of dopamine uptake is performed using synaptosomes isolated at Cerep in a 0.32 M sucrose buffer from a male Wistar rat striatum. The uptake of radiolabelled dopamine by synaptosomes (20 µg of proteins/point) is allowed by incubating them for 15 minutes at 37° C. in presence of test compounds and [3H]-dopamine (0.1 µCi/point). The experiment is performed in a deep well. Synaptosomes and [3H]-dopamine are prepared in a Krebs buffer pH 7.4 containing 25 mM NaHCO$_3$, 11 mM glucose and 50 µM ascorbic acid. This incubation buffer is oxygenated during 5 minutes before incubation. Basal control is incubated for 15 minutes at 4° C. in order to avoid any uptake. Following this incubation the uptake is stopped by filtration through an "unifilter 96-wells GFB " Packard plate washed with Krebs buffer containing 25 mM NaHCO$_3$ in order to eliminate the free [3H]-dopamine. The radioactivity associated to the synaptosomes retained onto the unifilter corresponding to the uptake is then measured with a microplate scintillation counter Topcount, Packard using a scintillation liquid microscint 0, Packard. The reference compound is GRB 12909 tested at 8 concentrations ranging from $10^{-11}$ M to $10^{-6}$ M in order to obtain an IC$_{50}$ value. [See Jankowsky et al. "Characterization of sodium-dependent [3H]GBR-12935 binding in brain: a radioligand for selective labeling of the dopamine transport complex." Journal of Neurochemistry. 46 (4): 1272–1276 (1986).]

Norepinephrine Uptake Functional Assay

Characterization of norepinephrine uptake is performed using synaptosomes isolated at Cerep in a 0.32 M sucrose buffer from a male Wistar rat hypothalamus. The uptake of radiolabeled norepinephrine by synaptosomes (100 µg of proteins/point) is allowed by incubating them for 20 minutes at 37° C. in presence of test compounds and [3H]-norepinephrine (0.1 µCi/point). The experiment is performed in a deep well.

Synaptosomes and [3H]-norepinephrine are prepared in a Krebs buffer pH 7.4 containing 25 mM NaHCO$_3$, 11 mM glucose and 50 µM ascorbic acid. This incubation buffer is oxygenated during 5 minutes before incubation. Basal control is incubated for 20 minutes at 4° C. in order to avoid any uptake. Following this incubation the uptake is stopped by filtration through an "unifilter 96-wells GFB " Packard plate washed with Krebs buffer containing 25 mM NaHCO$_3$ in order to eliminate the free [3H]-norepinephrine. The radioactivity associated to the synaptosomes retained onto the unifilter corresponding to the uptake is then measured with a microplate scintillation counter Topcount, Packard using a scintillation liquid microscint 0, Packard.

The reference compound is imipramine tested at 13 concentrations ranging from $10^{-11}$ M to $10^{-5}$ M in order to obtain an IC$_{50}$ value. [See Perovics and Müller, op.cit. (1995).]

In general, (S)-hydroxynefazodone of optical purity greater than 90% would be desirable, greater than 95% would be preferred, and greater than 98% is optimal. The results, employing enantiomers of greater than 98% optical purity, are shown in the following tables:

TABLE 1

Effect of Nefazodone and Hydroxy-Metabolites on Dopamine Receptor Binding (IC$_{50}$ Values, nM)

|  | D$_1$ | D$_2$ | D$_3$ | D |
| --- | --- | --- | --- | --- |
| Nefazodone | 1,980 | 716 | 2,240 | 495 |
| (RS)—OH | 2,270 | 1,420 | 2,560 | 1,310 |
| (R)—OH | 1,690 | 1,690 | 3,490 | 1,910 |
| (S)—OH | 2,310 | 788 | 1,910 | 994 |

TABLE 2

Effect of Nefazodone and Hydroxy-Metabolites on Serotonin Receptor Binding (IC$_{50}$ Values, nM)*

|  | 5-HT$_{1A}$ | 5-HT$_{1B}$ | 5-HT$_{1D}$ | 5-HT$_{2A}$ | 5-HT$_{2B}$ | 5HT$_{2C}$ | 5-HT$_{5A}$ | 5-HT$_6$ | 5-HT$_7$ |
|---|---|---|---|---|---|---|---|---|---|
| Nefazodone | 625 | 1,870 | 925 | 21 | 56 | 43 | 1,560 | 590 | 71 |
| (RS)-OH | 409 | 4,550 | 1,150 | 20 | 34 | 46 | 2,230 | 856 | 61 |
| (R)-OH | 496 | 3,610 | 1,990 | 22 | 28 | 33 | 2,040 | 1,020 | 71 |
| (S)-OH | 249 | 2,840 | 234 | 18 | 41 | 34 | 1,970 | 489 | 60 |

*Inactive on 5HT$_4$

TABLE 3

Evaluation of Nefazodone and Hydroxy-Metabolites as inhibitors of CYP45O

|  | Nef | R—OH—Nef | S—OH—Nef |
|---|---|---|---|
| CYP1A2 | >200 | >200 | >200 |
| CYP2C8 | 48 | 6 | 23 |
| CYP2C9 | 13 | 21 | 20 |
| CYP2C19 | 20 | 64 | >200 |
| CYP2D6 | 2 | 2 | 2 |
| CYP3A4 BFC | 0.2 | 0.2 | 0.2 |
| CYP3A4 BZRes | 2.2 | >200 | 3 |

TABLE 4

Effect of Nefazodone and Hydroxy-Metabolites on α$_1$ Receptor Binding and Monoamine Neuronal Transport (IC$_{50}$ Values, nM)

|  | Alpha$_1$ | 5-HT uptake | NE uptake |
|---|---|---|---|
| Nefazodone | 306 | 200 | 1,200 |
| (RS)—OH | 381 | 500 | 1,000 |
| (R)—OH | 367 | 640 | 1,200 |
| (S)—OH | 419 | 790 | 1,500 |

As shown in Table 4, racemic hydroxynefazodone and both of its enantiomers are significantly less active than nefazodone in inhibiting serotonin uptake. As shown in Table 2, all three hydroxynefazodones have high affinity for 5HT2A receptors, at which they are antagonists (data not shown). As can also be seen from Table 4, (S)-hydroxynefazodone is the least active enantiomer in inhibiting serotonin uptake, and from Table 2 (S)-hydroxynefazodone has the highest affinity for 5HT2A receptors. (S)-Hydroxynefazodone also exhibits excellent affinity for the D2 receptor (Table 1), Therefore, the (S) enantiomer would be the preferred enantiomer to employ.

EXAMPLE 1

Tablets
Composition per tablet:

| (S)-hydroxynefazodone | 25 mg |
|---|---|
| croscarmellose | 60 mg |
| colloidal silicon dioxide | 8 mg |
| magnesium stearate | 1 mg |
| microcrystalline cellulose | 190 mg |
| croscarmellose | 15 mg |
| talc | 10 mg |
| Total | 534 mg |

The (S)-hydroxynefazodone and silicon dioxide are dry mixed, the first portion of croscarmellose is added and the mixture is further dry mixed. The magnesium stearate is added, dry mixed and the mixture is run through a roller compactor and mill. The resulting dry granulate is mixed with the remaining three ingredients and compressed into tablets.

Powder-filled Capsules
Composition per unit dosage:

| (S)-hydroxynefazodone | 200 mg |
|---|---|
| lactose | 250 mg |
| corn starch | 60 mg |
| magnesium stearate | 5 mg |

The hydroxynefazodone, lactose and cornstarch, in the proportions shown above, are blended until uniform and then the magnesium stearate is blended into the resulting powder, which is sieved and filled into suitably sized, two-piece, hard gelatin capsules using conventional machinery. Other doses may be prepared by altering the fill weight and, if necessary, changing the capsule size to suit.

What is claimed is:

1. A method for treating psychosis in a human comprising administering to a person a therapeutically effective amount of (S)-hydroxynefazodone, substantially free of its (R)-stereoisomer, or a pharmaceutically acceptable salt thereof.

2. A method according to claim 1 wherein said psychosis is mania or bipolar disorder.

3. A method according to claim 1 wherein said psychosis is schizoaffective disorder.

4. A method according to claim 1 wherein said psychosis is schizophrenia.

5. A method according to claim 1 wherein said psychosis is dementia.

6. A method according to claim 1 wherein said psychosis is obsessive-compulsive disorder.

7. A method according to claim 1 wherein said psychosis is Tourette's disorder.

* * * * *